(12) United States Patent
Mustapha

(10) Patent No.: US 10,980,552 B2
(45) Date of Patent: Apr. 20, 2021

(54) REENTRY CATHETER WITH EXPANDING ANCHORS

(71) Applicant: Jihad Mustapha, Ada, MI (US)

(72) Inventor: Jihad Mustapha, Ada, MI (US)

( * ) Notice: Subject to any disclaimer, the term of this patent is extended or adjusted under 35 U.S.C. 154(b) by 307 days.

(21) Appl. No.: 15/949,765

(22) Filed: Apr. 10, 2018

(65) Prior Publication Data

US 2018/0289382 A1    Oct. 11, 2018

Related U.S. Application Data

(60) Provisional application No. 62/483,597, filed on Apr. 10, 2017.

(51) Int. Cl.
| | |
|---|---|
| *A61B 17/22* | (2006.01) |
| *A61B 17/34* | (2006.01) |
| *A61B 17/3207* | (2006.01) |
| *A61M 25/00* | (2006.01) |
| *A61B 90/00* | (2016.01) |
| *A61M 25/01* | (2006.01) |
| *A61M 25/02* | (2006.01) |

(52) U.S. Cl.
CPC ...... *A61B 17/22* (2013.01); *A61B 17/320758* (2013.01); *A61B 17/3415* (2013.01); *A61M 25/0194* (2013.01); *A61B 17/3478* (2013.01); *A61B 2017/22001* (2013.01); *A61B 2017/22038* (2013.01); *A61B 2017/22071* (2013.01); *A61B 2017/22094* (2013.01); *A61B 2017/22095* (2013.01); *A61B 2017/320733* (2013.01); *A61B 2090/0811* (2016.02); *A61B 2090/3966* (2016.02); *A61M 25/0136* (2013.01); *A61M 2025/0004* (2013.01); *A61M 2025/0197* (2013.01); *A61M 2025/0293* (2013.01)

(58) Field of Classification Search
CPC ............ A61B 17/22; A61B 17/320758; A61B 17/3415; A61B 17/3478; A61B 2017/22001; A61B 2017/22038; A61B 2017/22071; A61B 2017/22094; A61B 2017/22095; A61B 2017/320733; A61B 2090/0811; A61B 2090/3966; A61M 2025/0004; A61M 2025/0197; A61M 2025/0293; A61M 25/0136; A61M 25/0194

See application file for complete search history.

(56) References Cited

U.S. PATENT DOCUMENTS

| | | | | |
|---|---|---|---|---|
| 2014/0012281 | A1* | 1/2014 | Wang ................ | A61M 25/0023 606/108 |
| 2014/0194776 | A1* | 7/2014 | Gunday ............. | A61B 17/3478 600/567 |

OTHER PUBLICATIONS

Medtronic, Enteer Re-entry System, 2018, https://www.medtronic.com/us-en/healthcare-professionals/products/cardiovascular/chronic-total-occlusion-devices/enteer.html.

(Continued)

*Primary Examiner* — Mohamed G Gabr
(74) *Attorney, Agent, or Firm* — Standley Law Group LLP

(57) ABSTRACT

A reentry apparatus has an outer catheter configured to accommodate a first reentry device and an inner catheter configured to fit within the outer catheter. The inner catheter has a series of expanding anchors extending from the outer surface of the inner catheter and a reentry channel configured to accommodate a second reentry device. A retaining wire extends along the upper surface of the expanding anchors. A reentry channel is located in the configured to accommodate a second reentry device.

18 Claims, 13 Drawing Sheets

(56) References Cited

OTHER PUBLICATIONS

Medtronic, Crossing Portfolio Brochure, 2016.
Boston Scientific, OffRoad Re-entry Catheter System, 2017, https://www.bostonscientific.com/en-US/products/cto-systems/offroad-reentry-catheter.html.
Cordis, Outback Ltd Re-Entry Catheter, 2017, https://emea.cordis.com/emea/endovascular/lower-extremity-solutions/cross/outback-ltd-re-entry-catheter.html.
Philips, Pioneer Plus, IVIS-guided re-entry catheter, 2018, https://www.usa.philips.com/healthcare/product/HCIGTDPPLUS/pioneer-plus-ivusguided-reentry-catheter.
Covidien, Enteer Re-entry System, 2017.
Johnson & Johnson, Outback Re entry Catheter, Oct. 31, 2013, https://www.youtube.com/watch?v=9yfcqE5kRk.
Philips Volcano, Pioneer Plus IVUS Re-Entry Catheter, May 12, 2016, https://www.youtube.com/watch?v=o-v8EYaQSEI.

* cited by examiner

REENTRY CATHETER WITH EXPANDING ANCHORS

CROSS-REFERENCE TO RELATED APPLICATION

This application claims the benefit of U.S. Provisional Patent Application Ser. No. 62/483,597 filed on Apr. 10, 2017, the disclosures of which are hereby incorporated by reference in their entirety.

TECHNICAL FIELD

Exemplary embodiments of the present invention generally relate to a catheter apparatus for performing intravascular procedures, such as but not limited to, reentries.

BACKGROUND AND SUMMARY OF THE INVENTION

Atherosclerosis, or hardening of the arteries, is a medical condition where atherosclerotic material (i.e., plaque) accumulates along the inner walls of a blood vessel. As plaque builds up, the blood vessel may become partially or completely blocked, leading to issues such as coronary heart disease, angina, carotid artery disease, peripheral artery disease, and chronic kidney pain. Sometimes blood clots form near the blockage, or a piece of the blockage breaks off, and travels through the person's vascular system, which can potentially result in a heart attack or a stroke. Various intervention devices and procedures have been developed to treat atherosclerosis and related issues. Many of these intervention devices are now designed for intravascular use so as to minimize the invasiveness of the procedure.

A common example is an angioplasty. During an angioplasty procedure, an intravascular device(s) is used to move a balloon through a persons' vascular system to the site of the blockage. Once appropriately positioned, the balloon is inflated to compress the surrounding plaque, thereby increasing the lumen available for blood flow. The balloon is then deflated and removed and oftentimes a stent is inserted to help keep the plaque in its newly compressed state. However, in some cases the plaque blockage is too large, which prevents the angioplasty balloon or other intervention device from being appropriately positioned to perform the treatment. In such cases the procedure must generally be aborted unless the blockage can be circumnavigated (i.e., crossed).

Chronic Total Occlusions ("CTOs") are one type of plaque blockage that often requires such crossing. CTOs are generally blockages classified as having a Thrombolysis In Myocardial Infarction ("TIMI") grade flow of 0 or 1; 0 (no perfusion) referring to the absence of any antegrade flow beyond a coronary inclusion, and 1 (penetration without perfusion) referring to a faint antegrade coronary flow beyond the occlusion, with incomplete filing of the distal coronary bed. Regardless, when a CTO or other serious plaque blockage is encountered, a reentry catheter may be used to cross the blockage.

Typically, the reentry catheter is advanced along a guidewire either through the blockage itself or into the layered walls of the blood vessel where it can then be advanced passed the blockage. Once the reentry catheter is sufficiently advanced through or past the blockage, a tool is used to reenter the true lumen of the blood vessel. Using the tool, the guidewire is advanced past the blockage and into the true lumen of the blood vessel. The reentry catheter is then typically removed and the desired intervention device may be advanced into position and used to treat the person. An example of such a device is the Outback® LTD® reentry catheter by Cordis® (https://emea.cordis.com/emea/endovascular/lower-extremity-solutions/cross/outback-ltd-re-entry-catheter.html).

Known devices, however, can be difficult and cumbersome to operate. They may require precise positioning and movement to perform the reentry procedure and may not be particularly stable. Further, known devices may provide only one reentry port configured to accommodate a single reentry device at a single angle. This can be particularly problematic as unpredictable wall thicknesses, blockage positioning, material compositions, and calcification densities can require differently positioned, sized, and types of reentry devices to perform a successful cross. Therefore, what is needed is a reentry catheter that is easy to use and provides multiple reentry ports for multiple reentry devices.

The present invention is a reentry catheter that is easy to use and provides multiple reentry ports for multiple reentry devices. The reentry catheter may comprise an outer catheter tube surrounding an inner catheter, both extending from a handle assembly. The inner catheter may be configured to normally remain substantially in line with the outer catheter, but upon removal from the outer catheter, revert to a pre-shaped state wherein the distal portion of the inner catheter is bent at an angle.

A series of expanding anchors may be located long the outer wall of the inner catheter and when the inner catheter is located inside of the outer catheter, the expanding anchors may be placed in a compressed state. However, once positioned at a treatment site, the inner catheter may be advanced relative to the outer catheter, thus exposing some or all of the expanding anchors. The expanding anchors may expand against the blood vessel wall, stabilizing the device and forcing the distal portion of the inner catheter towards a reentry target. Once appropriately positioned, a user of the device may advance a first or a second reentry device through one of two reentry apertures the inner catheter. Preferably, a first reentry aperture is located on the distal end of the inner catheter and a second reentry aperture is located along the side wall of the inner catheter such that the first and the second reentry device exit the inner catheter at different angles.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein.

DETAILED DESCRIPTION OF EXEMPLARY EMBODIMENT(S)

Various embodiments of the present invention will now be described in detail with reference to the accompanying drawings. In the following description, specific details such as detailed configuration and components are merely provided to assist the overall understanding of these embodiments of the present invention. Therefore, it should be apparent to those skilled in the art that various changes and modifications of the embodiments described herein can be made without departing from the scope and spirit of the present invention. In addition, descriptions of well-known functions and constructions are omitted for clarity and conciseness.

Figure 1:
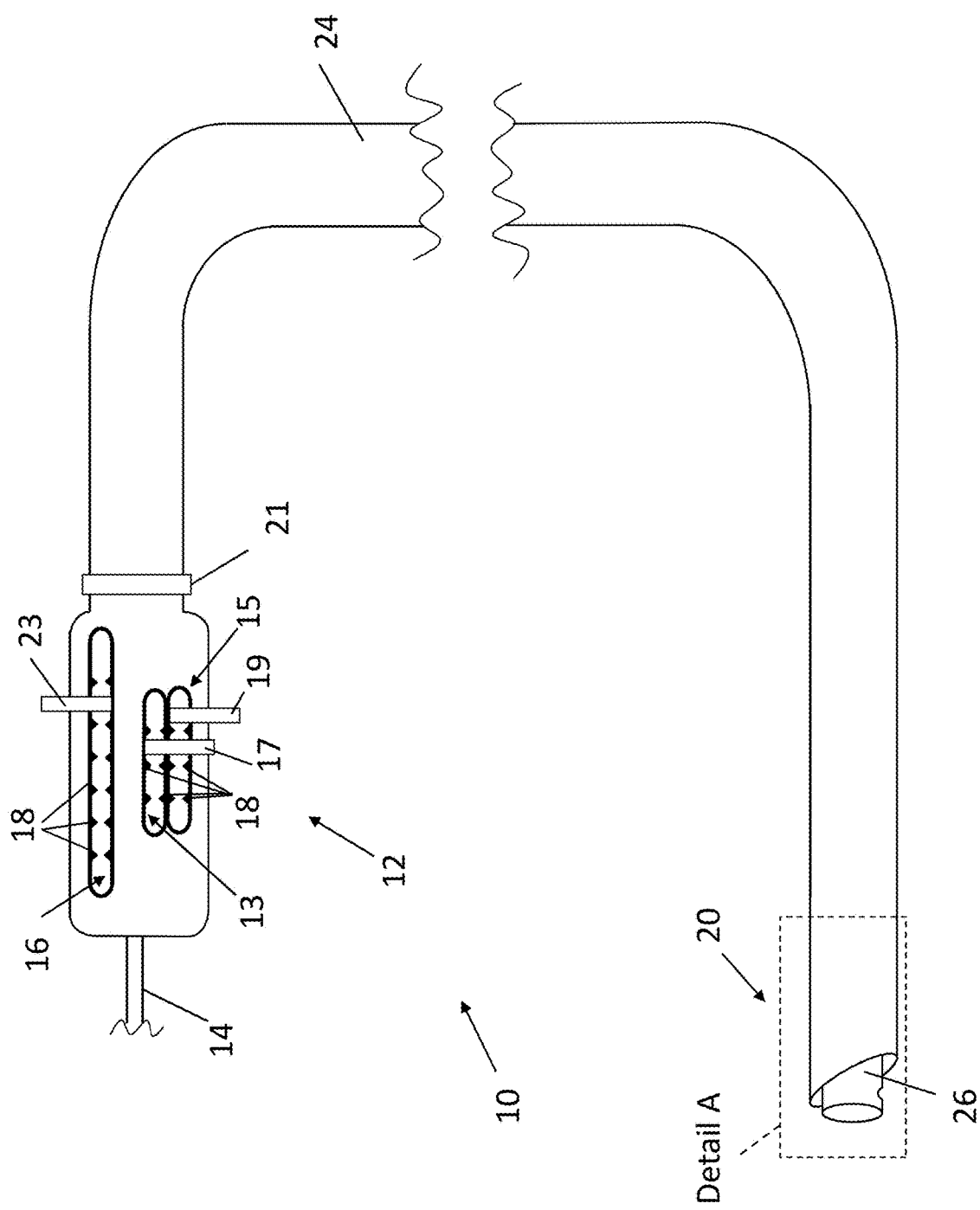
FIG. 1 is a plan view of an exemplary reentry catheter in accordance with the present invention and indicating detail A.

FIG. 1 is a plan view of an exemplary reentry catheter 10 in accordance with the present invention, also indicating detail A. The reentry catheter 10 may comprise a handle assembly 12 connected to an outer catheter 24. The outer catheter 24 may be tubular in shape and may be sufficiently flexible to navigate the sinuous passages of the human vascular system. In exemplary embodiments of the present invention, the handle assembly 12 may be connected to the outer catheter 24 by way of an attachment member 21. The attachment member 21 may be configured to permit the outer catheter 24 to move rotationally relative to the handle assembly 12. Otherwise, the handle assembly 12 may be integrally formed with, adhered to, bonded with, or otherwise attached to the outer catheter 24.

The outer catheter 24 may extend from the handle assembly 12 to a distal end portion 20. An inner catheter 26 may be positioned within the outer catheter 24 and may be substantially concentric therewith. The inner catheter 26 may also be tubular in shape and may be sufficiently flexible to navigate the sinuous passages of the human vascular system. A guidewire 14 may likewise be positioned within the inner catheter 26 and may be substantially concentric therewith. The guidewire 14 may likewise be tubular in shape and may be sufficiently flexible to navigate the sinuous passages of the human vascular system. The guidewire 14 may additionally pass through the handle assembly 12.

The handle assembly 12 may comprise various mechanisms for controlling the distal end portion 20 of the reentry catheter 10 and one or more reentry devices, such as a first reentry device 40 and a second reentry device 42, for the purposes described in greater detail herein. The first and second reentry devices 40 and 42 may be a needle, wire, transluminal catheter, or the like. Furthermore, the reentry devices 40 and 42 may be angled, straight, or otherwise pre-shaped. In this fashion, the first and second reentry devices 40 and 42 may be configured to reach separate reentry targets. The attachment member 21 may be used to orient the inner catheter 26 such that the first and second reentry devices 40 and 42 are aligned with the reentry target(s).

In exemplary embodiments of the present invention, the handle assembly 12 may comprise a groove 16 having a number of protrusions 18 located along the groove 16 at regular intervals. A control member 23 may be located within, and protrude from, the groove 16 and be configured to selectively frictionally engage the protrusions 18 so as to temporarily secure the control member 23 at a given location. The control member 23 may be in communication with the inner catheter 26 and may be configured to control movement of the inner catheter 26 relative to the outer catheter 24 as will be described in greater detail herein.

Similarly, the handle assembly 12 may further comprises a second groove 13 and a third groove 15, each having a series of protrusions 18 for selective frictional engagement with a second control member 17 and a third control member 19 located in each, respectively. The second control member 17 may be located within, and protrude from, the second groove 13 and may be in communication with the first reentry device 40. The third control member 19 may similarly be located within, and protrude from, the third groove 15 and may be in communication with the second reentry device 42. The second and third control members 17 and 19 may be configured to control movement of the first and second reentry device 40 and 42, respectively, as will be described in greater detail herein.

The advancement of the reentry device 40 and 42 may be limited by the second or third control members 17 and 19, respectively, or by the length or range of the first or the second reentry devices 40 and 42 themselves. In exemplary embodiments of the present invention, the first or the second reentry devices 40 and 42 have a range of 4 mm, 5 mm, 10 mm, and 15 mm, reached by moving the second and third control members 17 and 19 each respective protrusion 18 in the second and third grooves 13 and 15. However, any length or range of the first and second reentry devices 40 and 42 at any number or length intervals is contemplated. Furthermore, protrusions in the second and third grooves 13 and 15 may not be required such that the user can fluidly operate the second and third control members 17 and 19 any range.

It is notable that the control member 23, second control member 17, and third control member 19 may be any of type, style, size, or shape such as, but not limited to, a knob, dial, button, slider, lever, member, or the like. They may interact directly with the inner catheter 26, first reentry device 40, and second reentry device 42, respectively, or may do so through an intermediary such as, but not limited to, linkages, members, gears, levers, cams, shafts, motors, wiring, electrical controls, and the like.

The inner catheter 26, outer catheter 24, and other components of the reentry catheter 10 may be comprised of a metallic, polymer, or other suitable biocompatible material. The inner catheter 26, outer catheter 24, and other components of the reentry catheter 10 may be comprised of the same or different materials.

Figure 2:
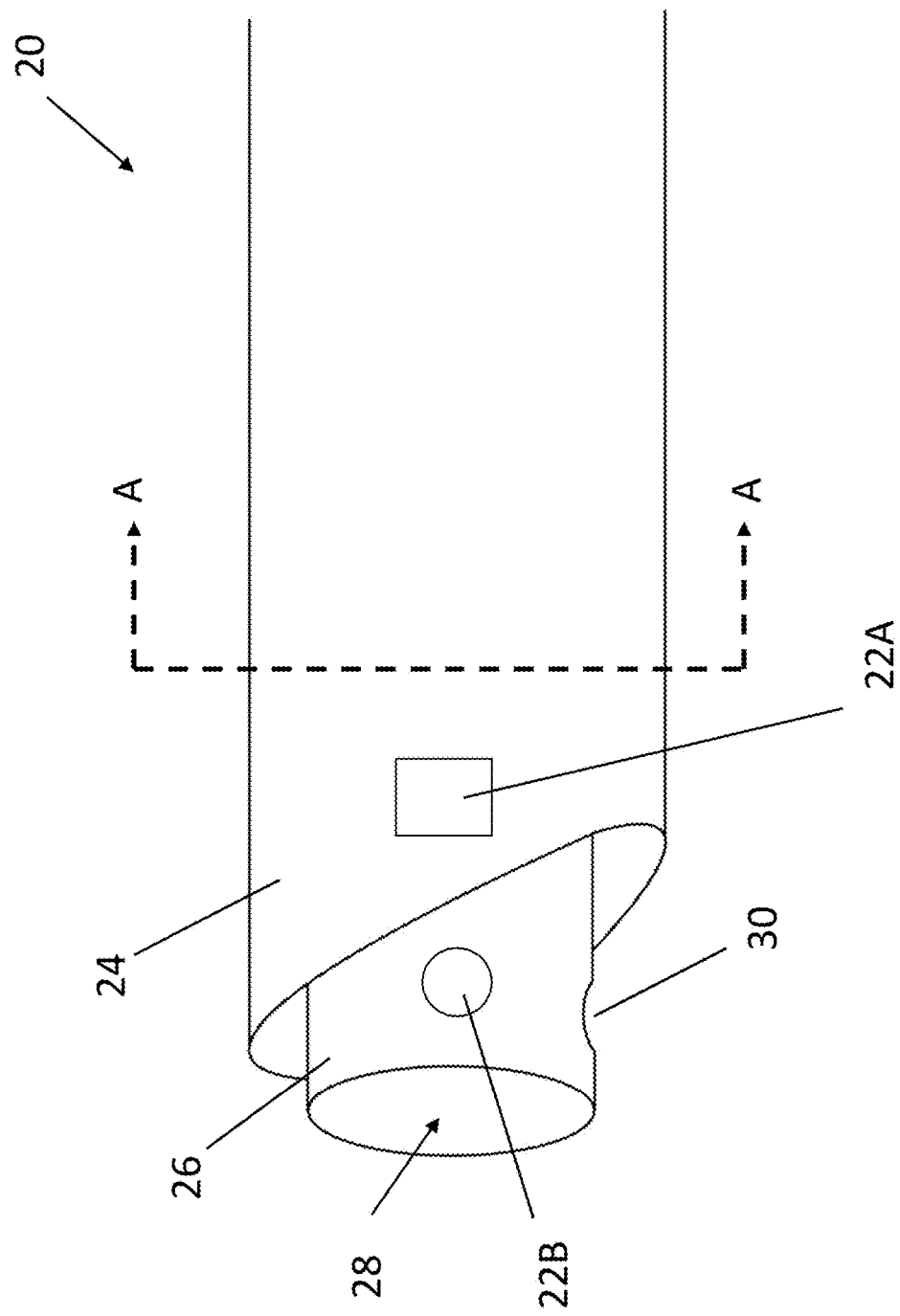
FIG. 2 is a detailed side view of detail A of FIG. 1 illustrating the distal end of the reentry catheter and further indicating section line A-A.

FIG. 2 is a detailed side view of detail A of FIG. 1, illustrating the distal end portion 20 of the reentry catheter 10. The inner catheter 26 is shown retracted relative to the outer catheter 24, though the inner catheter 26 may be further retracted such that it resides entirely within the outer catheter 24. The outer catheter 24 and the inner catheter 26 may comprise one or more radiopaque markers 22A and 22B. In exemplary embodiments of the present invention, the outer catheter 24 may have a single radiopaque marker 22A located near an end thereof and the inner catheter 26 may have a number of radiopaque markers 22B located beginning near the distal portion thereof and continuing along a length thereof. In exemplary embodiments of the present invention, the radiopaque markers 22A located on the outer catheter 24 are sufficiently distinguishable from the radiopaque markers 22B located on the inner catheter 26 such that a user of the reentry catheter 10 may determine how far the inner catheter 26 is extended relative to the outer catheter 24 as well as the angle and vertical position of the distal tip of the inner catheter 26 relative to the distal tip of the outer catheter 24. To accomplish this, for example but not to serve as a limitation, the radiopaque markers 22A located on the outer catheter 24 may be of a different shape than the radiopaque markers 22B located on the inner catheter 26. However, any number, size, or shape of radiopaque markers 22A an 22B at any number of locations is contemplated.

The distal portion of the inner catheter 26 may comprise a first reentry aperture 28 and a second reentry aperture 30. The first reentry aperture 28 may be located on the distal portion of the inner catheter 26. The second reentry aperture 30 may be located along the side wall of the inner catheter 26, a short distance from the distal tip thereof. In exemplary embodiments of the present invention, the second reentry aperture 30 is located approximately 2 mm from the distal tip of the inner catheter 26, though any location is contemplated. Also in exemplary embodiments of the present invention, the first and second reentry apertures 28 and 30 are configured to be set at different angles such that the corresponding reentry devices 40 and 42 exit the corresponding reentry apertures 28 and 30 at different angles. In this fashion, the first and second reentry device 40 and 42 may be configured to reach separate reentry targets.

Figure 3:
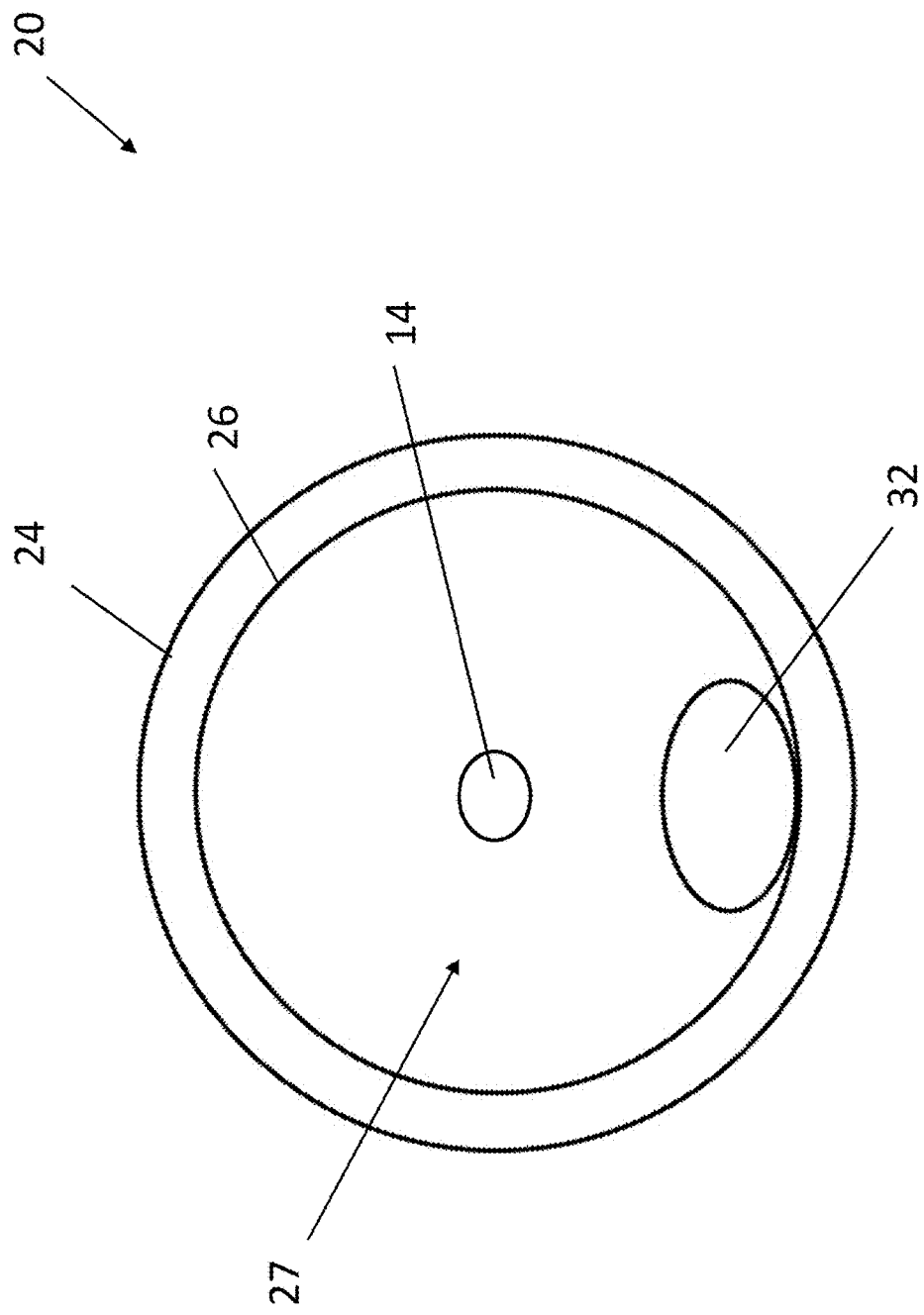
FIG. 3 is a front sectional view taken along section line A-A of FIG. 2.

FIG. 3 is a front sectional view taken along section line A-A of FIG. 2. The inner catheter 26 may be located substantially concentric with the outer catheter 24. The inner lumen 27 formed by the inner catheter 26 may also serve as the first reentry aperture 28. A reentry channel 32 may be located within the inner lumen 27 and is preferably oval shaped and positioned along the bottom of the inner lumen 27, though any shape and location is contemplated. The reentry channel 32 may provide stiffening and support to the inner and outer catheters 26 and 24. The reentry channel 32 may extend the length of the inner catheter 26 and the outer catheter 24 and may be sized and configured to accommodate the first reentry device 40 and the second reentry device 42 such that they do not inadvertently contact the inner or outer catheters 26 and 24. The guidewire 14 may be positioned to pass through the reentry channel 32. However, along some or all of the reentry catheter 10, the guide wire 14 may instead be positioned substantially concentric to the inner catheter 26.

Figure 4:
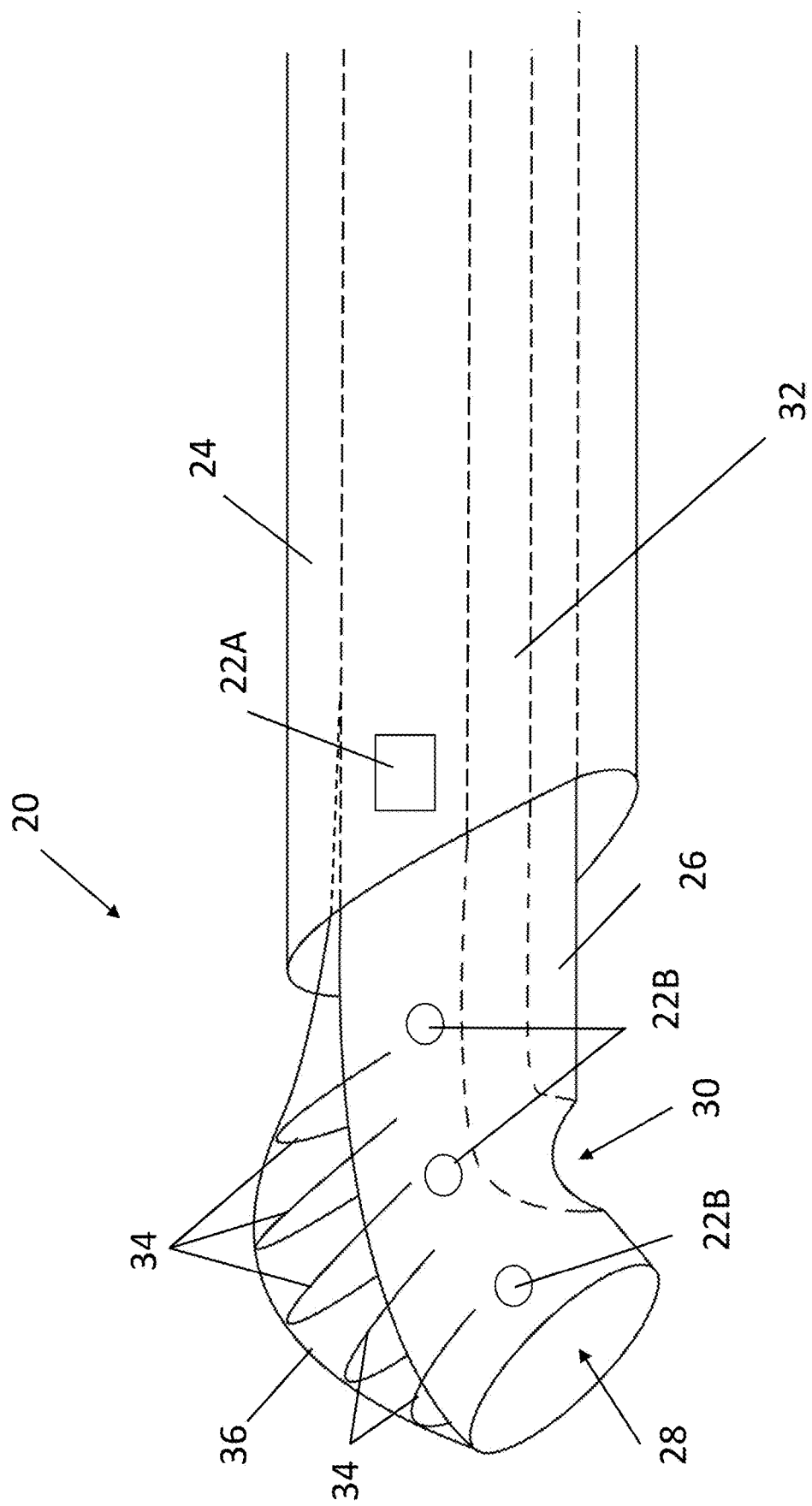
FIG. 4 is a detailed side view of the device of FIG. 2 illustrated with the inner catheter extended relative to the outer catheter.

FIG. 4 is a detailed side view of the device of FIG. 2 illustrated with the inner catheter 26 extended relative to the outer catheter 24. The inner catheter 26 may be pre-shaped by use of a memory material, weakened regions, resiliently deformable material, or the like, though such is not required. In exemplary embodiments of the present invention, the inner catheter 26 is pre-shaped such that the distal portion thereof deflects downward at substantially a 45-degree angle after being extended from the outer catheter 24, though any direction or angle of deflection is contemplated.

As the inner catheter 26 is extended relative to the outer catheter 24, one or more expanding anchors 34 may be exposed. The expanding anchors 34 may be crescent shaped and may be attached to the outer surface of the inner catheter 26. In exemplary embodiments of the present invention, the expanding anchors 34 may be biased in an expanded state such that the expanding anchors 34 automatically expand once removed from the outer catheter 24. The expanding anchors 34 may be comprised of a resiliently deformable material such as, but not limited to, nitinol. The expanding anchors 34 may be set at regular intervals along the outer surface of the inner catheter 26, though any number of expanding anchors 34 in any number of locations is contemplated.

A retaining wire 36 may run along the top of one or more of the expanding anchors 34 and be attached at the distal tip of the inner catheter 26 on one end and at a location on the inner catheter beyond the final expanding anchor 34 on a second end, though the retaining wire 36 may also be attached to one or more of the expanding anchors 34. The retaining wire 26 may serve to limit the expansion of the expanding anchors 34 thereby functioning as a safety device by preventing the expanding anchors 34 from expanding beyond their intended design. The retaining wire 36 may also function to keep the expanding anchors 34 evenly spaced apart.

In other exemplary embodiments of the present invention, movement of the inner catheter 26 relative to the outer catheter 24, and thus deployment or retraction of the expanding anchors 34, may be accomplished by pulling or pushing on the retaining wire 36, which may also act as a control line. In such embodiments, the retaining wire/control line 36 may run the length of the outer catheter 24 and may be in communication with the control member 23.

As previously explained, movement of the inner catheter 26 relative to the outer catheter 24 may be controlled by corresponding movement of the control member 23 located on the handle assembly 12 such that movement of the control member 23 is translated to movement of the inner catheter 26. Additionally, rotation of the inner catheter 26 relative to the outer catheter 24 may be accomplished by movement of the attachment member 21 or by another control mechanism. In exemplary embodiments of the present invention, movement of the control member 23 to each subsequent protrusion 18 on the groove 16 may result in sufficient movement of the inner catheter 26 so as to expose two additional expanding anchors 34.

The expanding anchors 34 may be configured to expand different amounts, which may be dictated by the length, attachment points, material characteristics, the like, or some combination thereof, of the expanding anchors 34. As the expanding anchors 34 may be constrained by the retaining wire 36, when all of the expanding anchors 34 are exposed, they may form a substantially curved profile. In exemplary embodiments of the present invention, the expanding anchors 34 may expand up to 8 mm, though it is contemplated that any number of the expanding anchors 34 may be expanded any amount.

When one or more of the expanding anchors 34 are exposed, and thus placed in the expanded state, the expanding anchors 34 may begin to push against the outer wall of a blood vessel 46 or other surrounding tissue, stabilizing the distal end portion 20 as well as forcing the distal tip of the inner catheter 26 to deflect downward towards the reentry target. As more expanding anchors 34 are exposed, the force on the distal portion of the inner catheter 26 may be increased, resulting in greater deflection of the distal tip of the inner catheter 26. In exemplary embodiments of the present invention, the exposure of each additional expanding anchor 34 corresponds to a 1 mm vertical drop of the distal tip of the inner catheter 26, though any distance is contemplated. The distal portion of the inner catheter 26 may be configured to deflect or drop a specified amount by the location and configuration of the expanding anchors 34, by pre-shaping the inner catheter 26, through the strategically located use of weakened regions, some combination thereof, or the like.

In other exemplary embodiments of the present invention, the expanding anchors 34 may be configured to expand an increasing amount as more of the inner catheter 26 is exposed, which may be configured to correlate with either an increased or a consistent vertical drop with the exposure of each additional expanding anchor 34. The amount of expansion and resulting force implemented by the expanding anchors 34 may be adjusted to any amount. In exemplary embodiments of the present invention, the amount of expansion and resulting force and vertical travel is adjusted to account for the anticipated resistance of the tissue to be reentered or the reentry targets to be accessed.

The guidewire 14, outer catheter 24, and inner catheter 26 may be of any length, size, and shape. In fact, the size, length, and/or shape of the guidewire 14, outer catheter 24, and inner catheter 26 may be adjusted to perform various procedures with the reentry catheter 10. However, in exemplary embodiments of the present invention, the first reentry aperture 28 and the inner lumen 27 may have an internal diameter of 0.35 inches and the inner catheter 26 may have an outer diameter of 0.46 inches (including the expanding anchors 34 when in the compressed state). The outer catheter 24 may have an outer diameter of 0.5 inches and an inner diameter of 0.48 inches. The reentry channel 32 and the second reentry aperture 30 may have an inner diameter of 0.16 inches or be sized and configured to accommodate a 0.14-0.18 inch diameter reentry device, wire, needle, transluminal catheter, or other tool. These measurements are merely exemplary and are not intended to be limiting. Any size or shape for the reentry catheter 10 and its various components is contemplated.

Figure 5:
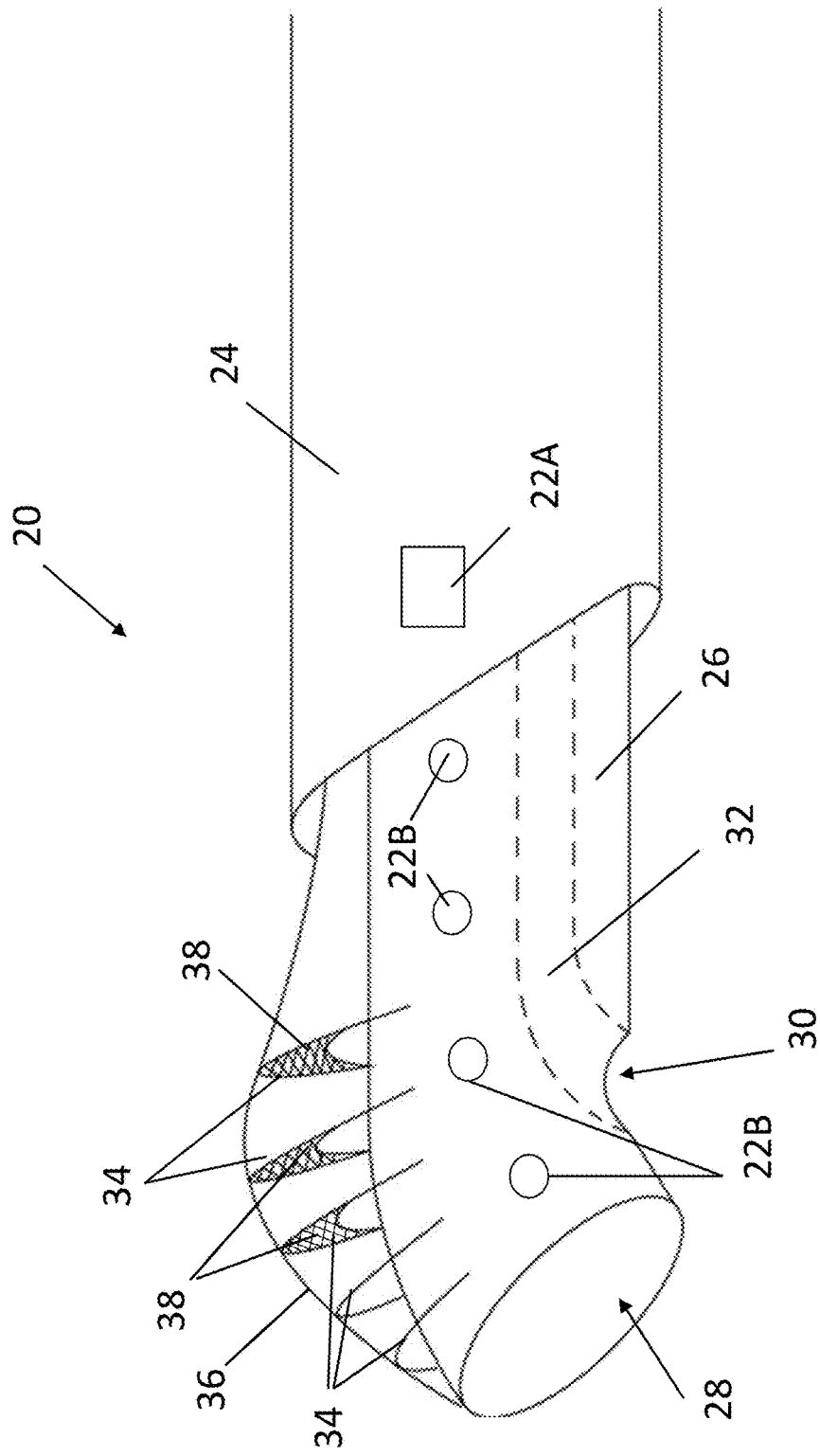
FIG. 5 is a detailed side view similar to FIG. 4, illustrating another exemplary embodiment of the reentry catheter.

FIG. 5 is a detailed side view similar to FIG. 4, illustrating another exemplary embodiment of the reentry catheter 10 wherein one or more of the expanding anchors 34 further comprises a webbing 38 located within the arch formed by the expanding anchors 34. The webbing 38 may be comprised of a metallic, such as but not limited to, a nitinol mesh. The webbing 38 may be configured to provide additional structural support and stability and may additionally assist in controlling the expansion of the expanding anchors 34.

Figure 6:
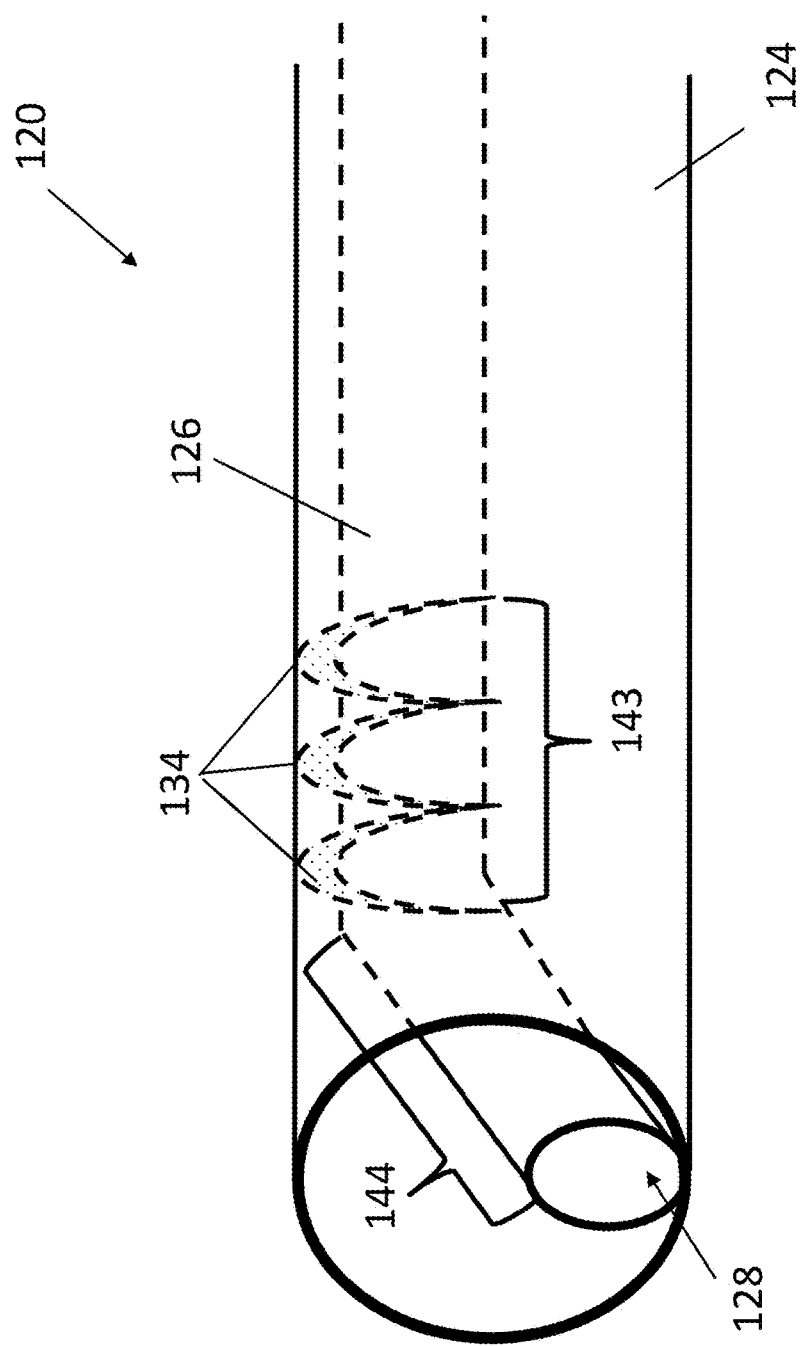
FIG. 6 is a detailed side view of another exemplary embodiment of the reentry catheter.
Figure 7:
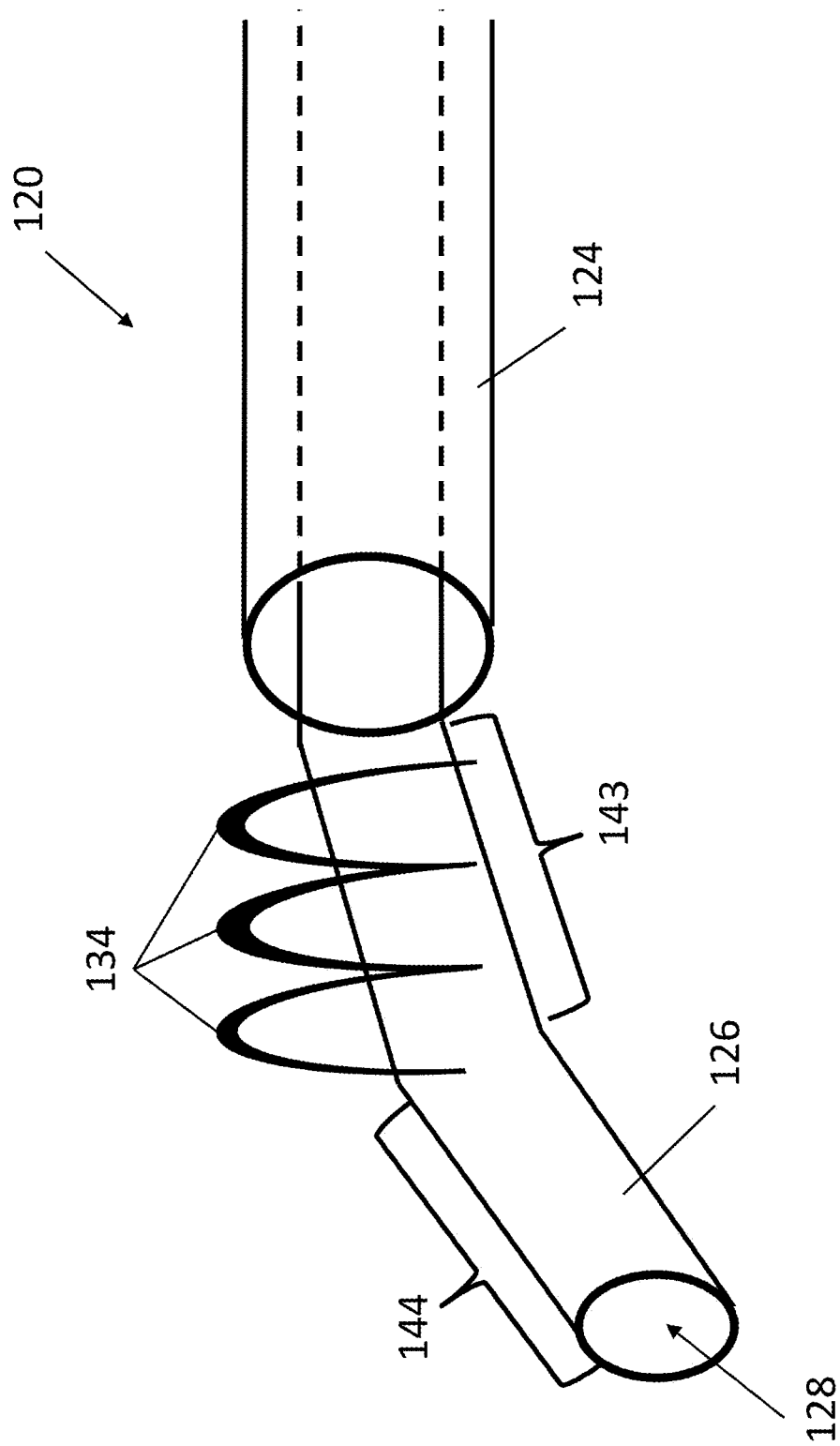
FIG. 7 is a detailed side view of the device of FIG. 6 illustrated with the inner catheter extended relative to the outer catheter.

FIG. 6 and FIG. 7 illustrate another exemplary embodiment of a distal end portion 120 of the reentry catheter 10 where similar features are numbered similarly (i.e., 26 and 126). In this exemplary embodiment of the present invention, a section 144 of the distal end portion 120 may be formed at an angle. For example, but not to serve as a limitation, the angled section 144 of the distal end portion 120 may be integrally formed bend at a first location such that it is pre-shaped. The expanding anchors 134 may be located after the pre-shaped section 144. Any type or amount of pre-shaping is contemplated, including any direction, amount, or angle of bend.

As the inner catheter 126 is advanced relative to the outer catheter 124, and the expanding anchors 134 are thus removed from the inner catheter 126, the expanding anchors 134 may expand against the blood vessel 46 or other surrounding tissue, thereby forcing the inner catheter 126 to deflect downward over a second section 143 thereof which is located proximally relative to the first, pre-shaped section 144. The angle and direction of the bend along the second section 143 may be the same or different from the direction or angle of the pre-shaped section 144. Though the present embodiment is shown with a single pre-shaped section 144, any number of pre-shaped sections at any number of locations is contemplated.

Figure 8:
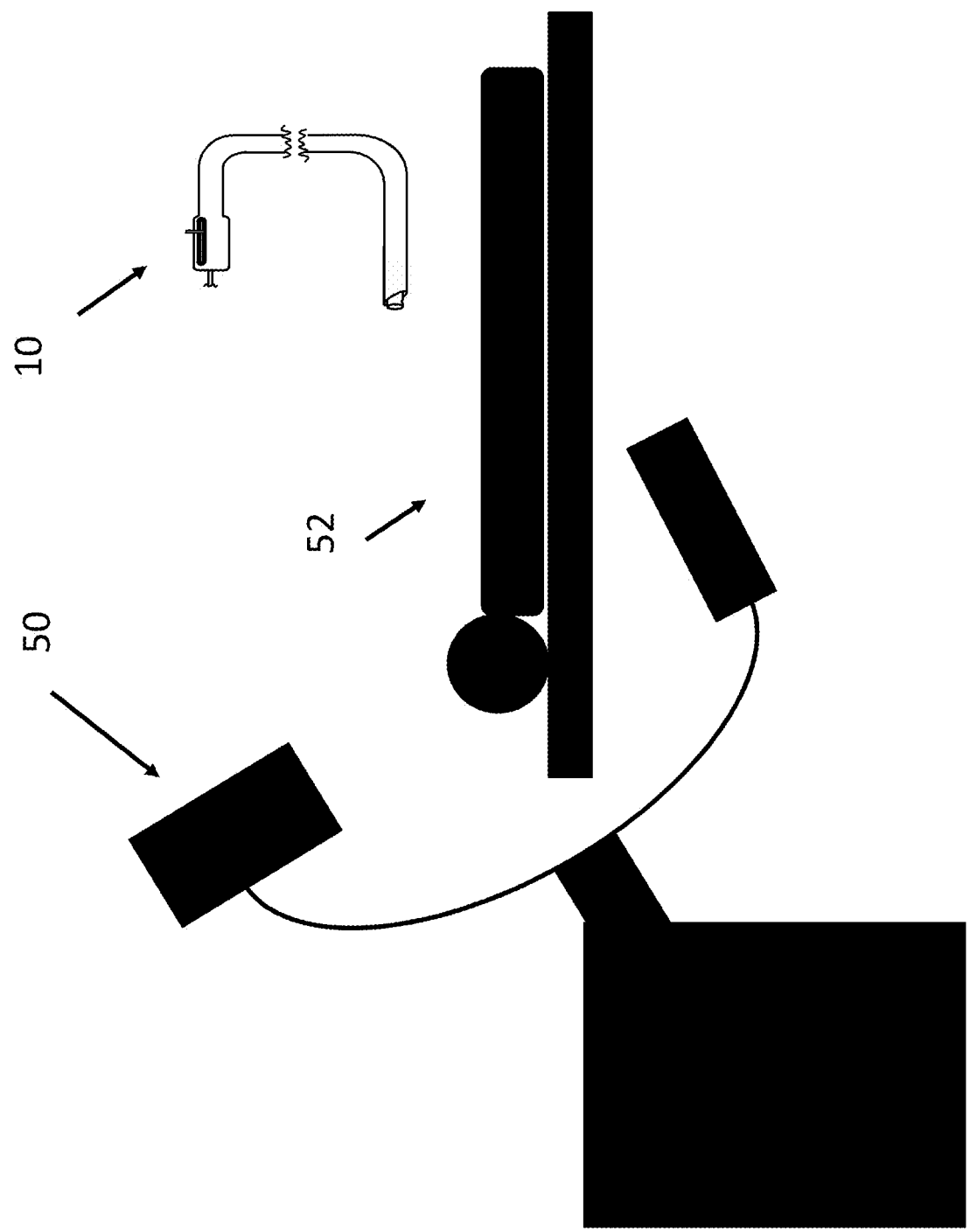
FIG. 8 is a plan view for an exemplary system utilizing the present invention.

FIG. 8 is a plan view for an exemplary system utilizing the present invention. A person 52 may be placed on a table for performing the procedure. An imaging device 50 may be positioned to periodically or continuously capture images of the reentry catheter 10 or the person's 52 vascular system. Such imaging devices 50 are known in the art and typically use fluoroscopy techniques so that the user of the reentry catheter 10 can monitor the location and movement of the reentry catheter 10, particularly by using the radiopaque markers 22A and 22B located thereon while performing the procedures shown and described herein.

As will be shown and described in greater detail herein, the guidewire 14 may initially be inserted intravascularly into the person 52. The guidewire 14 may be advanced through the person's 52 vascular system until it reaches a treatment site or until its pathway is impeded by a blockage 48. In exemplary embodiments of the present invention, multiple devices may be used along the same guidewire 14. In such cases, it may sometimes be necessary to remove the device currently being used on the guidewire 14 before inserting the reentry catheter 10. Regardless, the reentry catheter 10 may then be advanced along and beyond the guidewire 14 into or through at least a portion of the blockage 48. In other exemplary embodiments of the present invention, the reentry catheter 10 may instead be advanced along and beyond the guidewire 14 and into or through the surrounding layers 45 that form the wall of the blood vessel 46, or through other surrounding tissue, such that the reentry catheter 10 may circumnavigate the blockage 48. The inner catheter tube 26 may be rotated such that the first and second reentry apertures 28 and 30, and thus the projected path of the first and second reentry device 40 and 42, are aligned with the reentry target(s). Once positioned appropriately, the inner catheter tube 26 may be advanced relative to the outer catheter tube 24 by movement of the control member 23 on the handle assembly 12 such that appropriate number of expanding anchors 34 are exposed to deflect the distal end of the inner catheter 26 the appropriate amount, thereby positioning the first or second reentry apertures 28 and 30 to align the intended path of the first or second reentry devices 40 and 42 with the intended reentry target(s).

Next, the first or the second reentry devices 40 and 42 may be advanced through the first or second reentry apertures 28 and 30, respectively, using the second or third control members 17 and 19, respectively. The advancement of the reentry device 40 and 42 may be limited by the second or third control members 17 and 19, respectively, or by the length of the first or the second reentry devices 40 and 42 themselves. In exemplary embodiments of the present invention, the first or second reentry devices 40 and 42 are 4 mm in length, though any length is contemplated. The reentry devices 40 and 42 may pierce the blockage 48, the wall of the blood vessel 46, or the surrounding tissue such that the reentry device 40 or 42 reenters the true lumen of the blood vessel 46 or otherwise accesses the reentry target(s). Regardless, once the reentry device 40 or 42 is advanced beyond the blockage 48 (i.e., crossed), or the reentry target is accessed, the guide wire 14 may be advanced through the appropriate reentry device 40 or 42. Should one of the reentry apertures 28 or 30 not be properly positioned or one of the reentry device 40 or 42 be unable to perform the reentry, the other reentry aperture 28 or 30 and reentry device 40 or 42 may be utilized. This may be particularly advantageous as tissue resistance may vary by location. Alternatively, the first and second reentry apertures 28 and 30 and first and second reentry devices 40 and 42 may be utilized to reach two separate reentry targets.

Regardless, the reentry catheter 10 may then be removed and the appropriate intervention may be performed. However, in other exemplary embodiments of the present invention, the intervention is performed using the reentry catheter 10 by advancing appropriate tools therethrough. Such interventions may include, but are not limited to, trans-luminal, trans vascular to organs and trans-vascular transfers of vascular devices, drugs, target organ biopsy and selective angiography. The present invention is not limited to crossing CTOs, but may be used to cross any type of blockage or access any reentry target(s) as well as perform reentries related to any applicable procedures.

Figure 9:
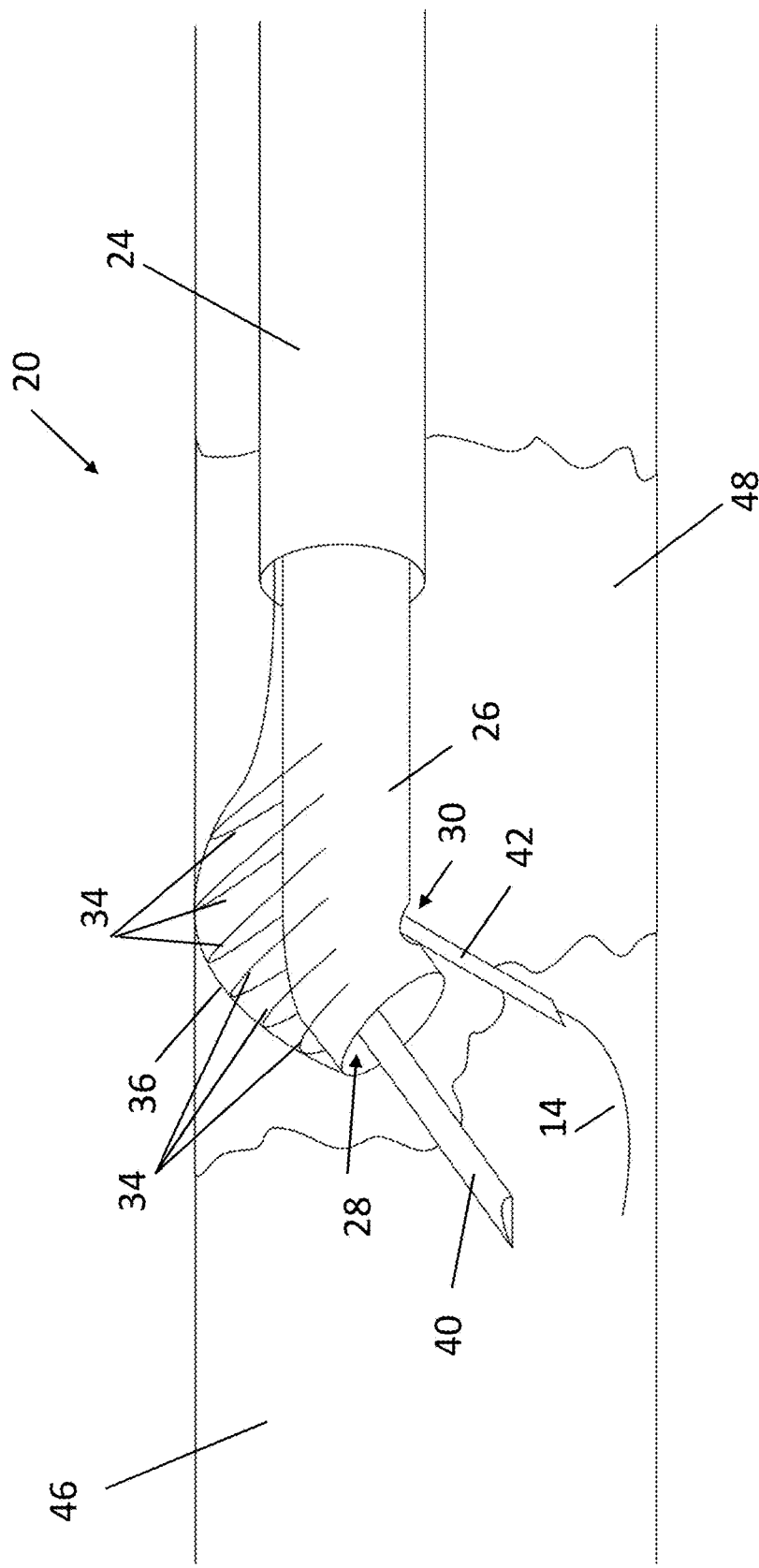
FIG. 9 is a detailed side view of the device of FIG. 4, illustrating an exemplary application of the present invention and technique for crossing a blockage in a blood vessel.

FIG. 9 is a detailed side view of the device of FIG. 4, illustrating the distal end of the reentry catheter 20 crossing a blockage 48 in a blood vessel 46 using an exemplary technique. In this exemplary embodiment, the reentry catheter 10 is advanced through at least a portion of the blockage 48. When the reentry catheter 10 is appropriately positioned or cannot be advanced further, the inner catheter 26 may be advanced relative to the outer catheter 24, thus deflecting the distal end of the inner catheter 26, and the reentry devices 40 or 42 may then be extended from the first or second reentry apertures 28 or 30 respectively until they reach beyond the blockage 48 into the true lumen of the blood vessel 46 or reach the reentry target(s). The guide wire 14 or other tool may then be advanced through the first or the second reentry device 40 or 42 and into the true lumen of the blood vessel 46, thus crossing the blockage 48. In another exemplary application, but not to serve as a limitation, the reentry catheter 10 may be used to pass through the wall of the blood vessel 46 and access neighboring organs to perform a biopsy. Regardless, the reentry catheter 10 may then be removed. If required, an intervention or other treatments may then be performed.

Figure 10:
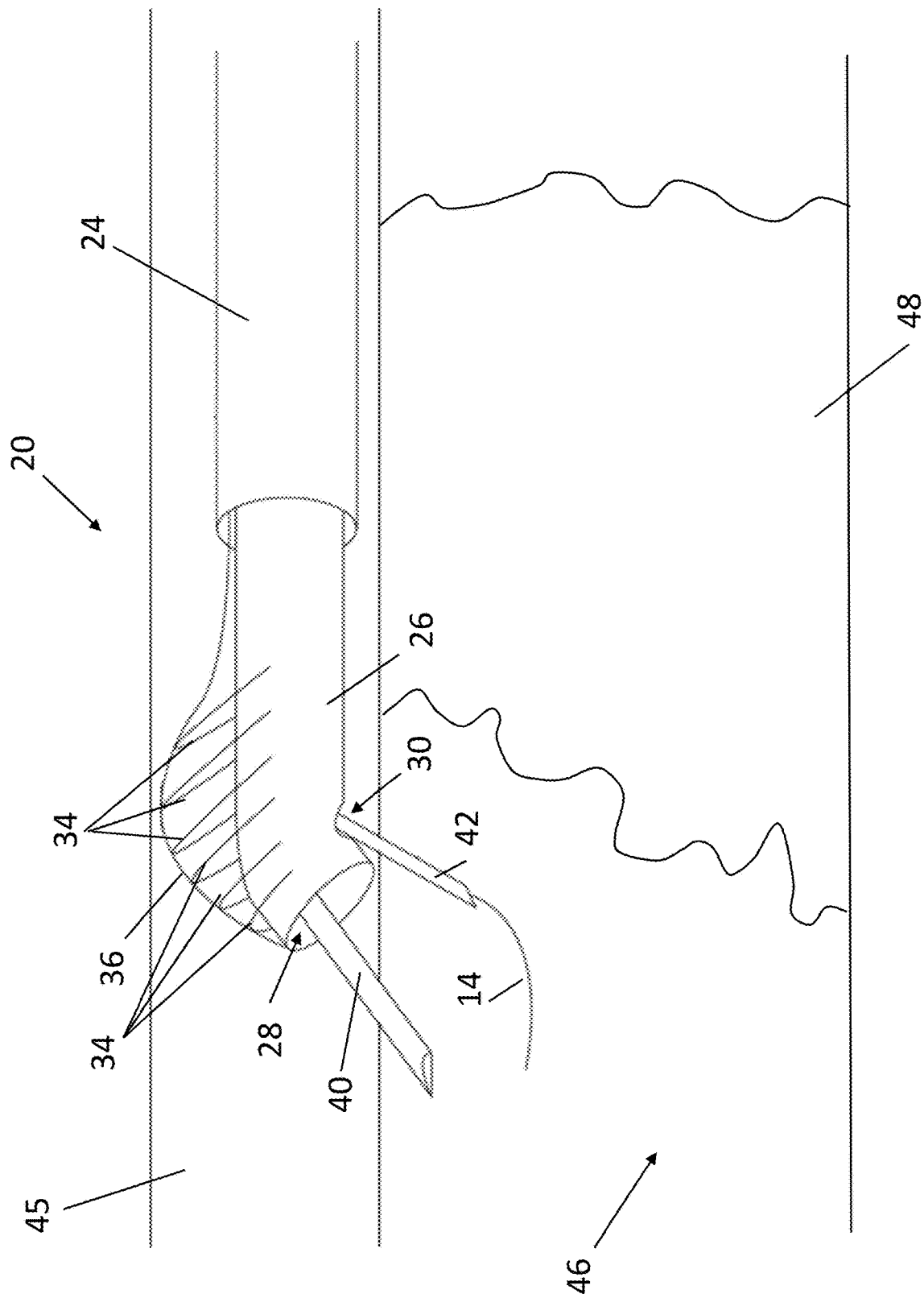
FIG. 10 is a detailed side view similar to FIG. 9, illustrating another exemplary application of the present invention and technique for crossing a blockage in a blood vessel.

FIG. 10 is a detailed side view similar to FIG. 9, illustrating how the reentry catheter 10 may alternatively be used to circumnavigate the blockage 48 using another exemplary technique. The distal end portion 20 of the reentry catheter 10 may be manipulated into the layers 45 that form the wall of the blood vessel 46. The distal end portion 20 may be advanced near or beyond the end of the blockage 48. The inner catheter 26 may be advanced relative to the outer catheter 24, thus deflecting the distal end of the inner catheter 26, and the reentry device 40 or 42 may then be extended from the first or the second reentry apertures 28 or 30, respectively, such that the first or the second reentry devices 40 and 42 may be extend into true lumen of the blood vessel 46. The guide wire 14 or other tool may then be advanced through the first or the second reentry device 40 or 42 and into the true lumen of the blood vessel 46, thus crossing the blockage 48. The expanding anchors 34 may be forced back into a collapsed state as the inner catheter 26 is retracted relative to the outer catheter 24. Once the inner catheter 26 is completely retracted, the reentry catheter 10 may be removed and the intervention or other treatment may proceed.

Figure 11:
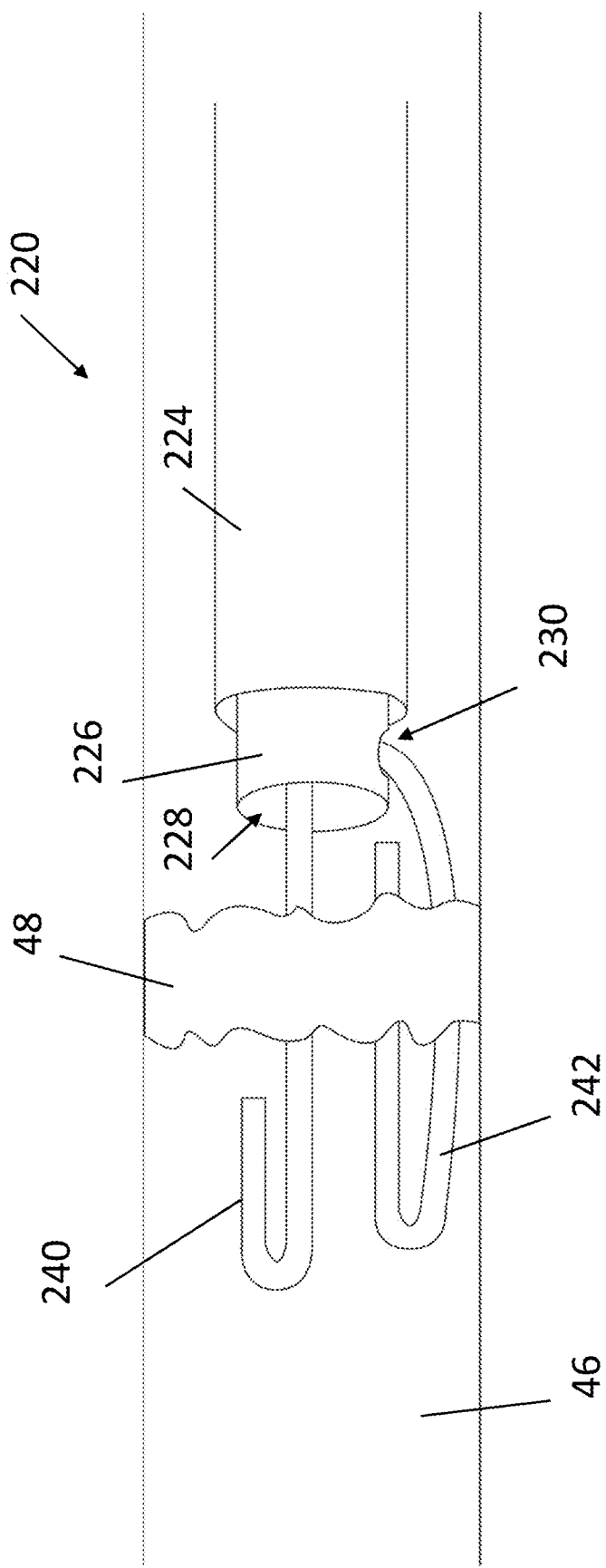
FIG. 11 is a detailed side view of another exemplary embodiment of the reentry catheter in another exemplary application and using another exemplary technique for crossing a blockage in a blood vessel.

FIG. 11 is a detailed side view of another exemplary embodiment of the distal end 220 of the reentry catheter 10 using another exemplary technique for crossing a blockage 48 in a blood vessel 46 where similar features are numbered similarly (i.e., 26 and 226). The distal end 220 may be used to cross blockages 48 such as, but not limited to, CTOs. The reentry devices 40 and 42 may be wires, boring tools, cutting devices, abrasive surfaces, or other tools configured to create a passage through the blockage 48. In such embodiments, the reentry devices 40 and 42 may be manipulated by rotation or other movement of the inner catheter 226 relative to the outer catheter 224. This may be accomplished, for example, by use of the attachment member 21 which may be in communication with the inner catheter 226 such that rotation of the attachment member 21 causes rotation of the inner catheter 226. For example, but not to serve as a limitation, one or more of the reentry device 40 and 42 may comprise a tapered tip having an abrasive outer surface. In this way, the reentry device 40 and 42 may be advanced relative to the distal end portion 220 while being rotated so as to bore through the blockage 48.

Figure 12A:
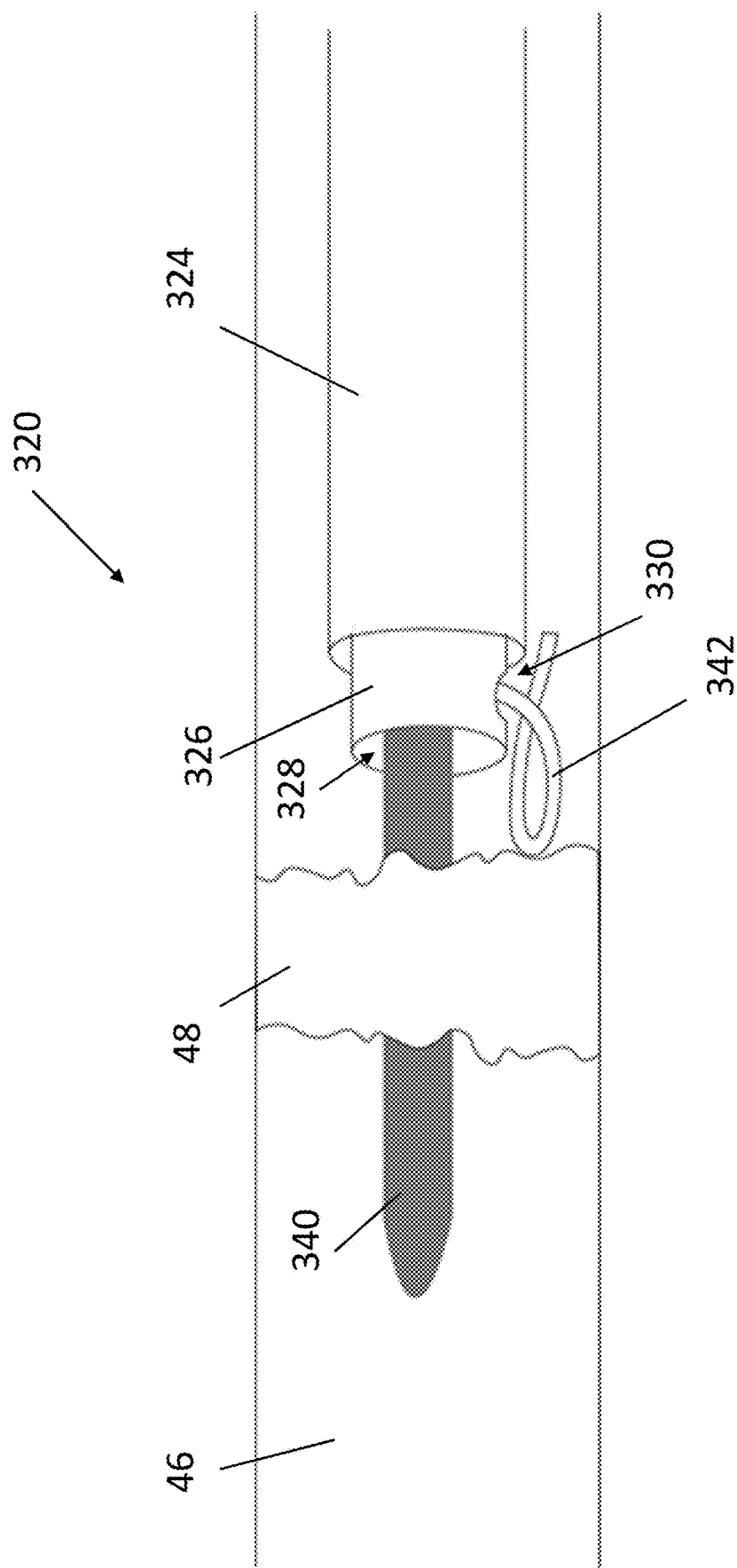
FIG. 12A is a detailed side view of another exemplary embodiment of the reentry catheter in another exemplary application and using another exemplary technique for crossing a blockage in a blood vessel.

FIG. 12A is a detailed side view of another exemplary embodiment of the distal end 320 of the reentry catheter 10 using another exemplary technique for crossing a blockage 48 in a blood vessel 46 where similar features are numbered similarly (i.e., 26 and 326). In this embodiment, the first reentry device 340 may have a large diameter and may be configured to bore through the blockage 48. This figure is intended to illustrate that any size reentry devices 340 or 342 may be utilized with the present invention. The first or the second reentry apertures 328 and 330 may be appropriately sized to fit said reentry devices 340 and 342.

Figure 12B:
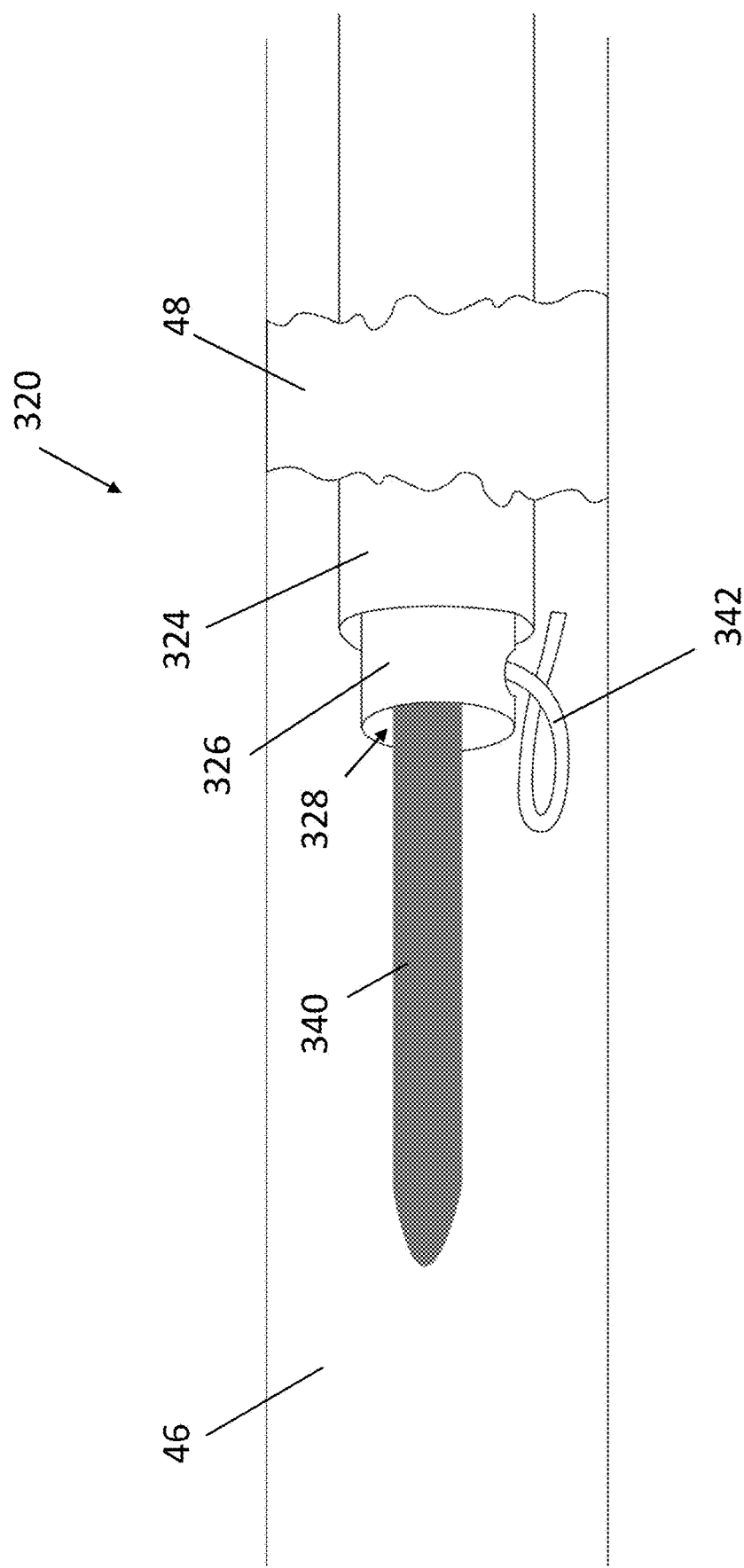
FIG. 12B is a detailed side view of the device of FIG. 12A after successfully crossing the blockage in the blood vessel.

FIG. 12B is a detailed side view of the device of FIG. 12A following a successful crossing of the blockage 48 in the blood vessel 46.

Any embodiment of the present invention may include any of the optional or preferred features of the other embodiments of the present invention. The exemplary embodiments herein disclosed are not intended to be exhaustive or to unnecessarily limit the scope of the invention. The exemplary embodiments were chosen and described in order to explain the principles of the present invention so that others skilled in the art may practice the invention. Having shown and described exemplary embodiments of the present invention, those skilled in the art will realize that many variations and modifications may be made to the described invention. Many of those variations and modifications will provide the same result and fall within the spirit of the claimed invention. It is the intention, therefore, to limit the invention only as indicated by the scope of the claims.

What is claimed is:

1. A reentry apparatus comprising:
   an outer catheter defining a first lumen; and
   an inner catheter locatable within said first lumen and defining a second lumen, wherein said inner catheter is configured for movement between a first position where a distal portion of said inner catheter is disposed within the outer catheter and a second position where said distal portion of the inner catheter is exposed, said inner catheter comprising:
   a series of expandable anchors located along, and extending from an outer surface of, the distal portion of the inner catheter, wherein each of said expandable anchors are configured for movement into an expanded position when said inner catheter is placed in said second position and the expandable anchors are exposed to force deflection of said distal portion of said inner catheter into an angled position relative to an adjacent portion of said inner catheter;
a retaining wire extending along an upper surface of each of the expandable anchors; and
a reentry device; and
a reentry channel extending through said distal portion and configured to accommodate the reentry device.

2. The apparatus of claim 1 wherein:
each of the expandable anchors comprise a resiliently deformable material;
the expandable anchors are located at spaced intervals along an outer surface of the inner catheter;
each of the expandable anchors are attached to the retaining wire;
the retaining wire is configured to limit the expansion of, and maintain the spacing of, the expandable anchors.

3. The apparatus of claim 2 wherein:
each of the expandable anchors are biased in the expanded position.

4. The apparatus of claim 3 wherein:
each of the expandable anchors define an arch shape when in the expanded position.

5. The apparatus of claim 4 further comprising:
a handle assembly; and
a control member located at the handle assembly and configured to cause movement of the distal portion of the inner catheter between the first and second positions, wherein the expanding anchors are configured for movement between a compressed position when the inner catheter is in the first position such that the expandable anchors fit within the outer catheter, and the expanded position when the inner catheter is in the second position such that the expandable anchors expand to form an arch shape.

6. The apparatus of claim 5 wherein:
the retaining wire extends from the control member along a length of the outer catheter such that expandable anchors are moveable between the first and second positions by pushing or pulling the retaining wire by way of the control member.

7. The apparatus of claim 1 further comprising:
a first radiopaque marker located on a distal end of the outer catheter; and
a plurality of radiopaque markers located along a distal end of the inner catheter.

8. The apparatus of claim 1 wherein:
the reentry channel is located at a lower portion of the inner catheter;
the expandable anchors are located at an upper portion of the inner catheter; and
the upper portion opposes the lower portion.

9. The apparatus of claim 8 wherein:
at least a distal end of the reentry channel is configured for deflection to an angle relative to a longitudinal axis of the inner catheter with deflection of said distal portion of said inner catheter.

10. The apparatus of claim 1 further comprising:
a handle assembly comprising a first set of controls configured to control the movement of the inner catheter between said first position and said second position; and
a second set of controls located on the handle assembly and configured to control the movement of the reentry device.

11. The apparatus of claim 1 further comprising:
webbing located at each of the expandable anchors and extending between a respective one of the expandable anchors and the outer surface of the inner catheter.

12. The apparatus of claim 1 further comprising:
a second distal portion of the inner catheter located adjacent to said distal portion, wherein said second distal portion is formed at a first, nonlinear angle relative to a remaining portion of the inner catheter.

13. The apparatus of claim 1 further comprising:
an additional reentry device, wherein said second lumen is configured to accommodate the additional reentry device.

14. The apparatus of claim 13 wherein:
the reentry device comprises a first needle;
the additional reentry device comprises a second needle; and
the first and second reentry devices are each configured to accommodate a guidewire.

15. A reentry apparatus comprising:
an outer catheter defining a first lumen;
a first reentry device;
an inner catheter disposed within said outer catheter and defining an inner lumen configured to accommodate said first reentry device, said inner catheter comprising:
  a series of expandable anchors provided along a distal portion of the inner catheter and configured for movement into an expanded position when exposed to form an arch and wherein each of said expandable anchors are configured to force said distal portion to deflect into an angled position when in said expanded position;
  a retaining wire extending along an upper surface of each of the expandable anchors;
  a second reentry device; and
  a reentry channel extending through said distal portion and configured to accommodate the second reentry device;
a handle assembly; and
a control member located at the handle assembly and connected to the inner catheter for controlling movement of the inner catheter relative to the outer catheter so as to selectively expose the expandable anchors for movement between a retracted position and the expanded position.

16. A reentry method comprising the steps of:
providing a reentry apparatus comprising an outer catheter configured to accommodate an inner catheter comprising a series of expandable anchors located along, and extending from, an outer surface of a distal portion of the inner catheter, a retaining wire extending along an upper surface of the expandable anchors, and a reentry channel extending through the distal portion of the inner catheter and configured to accommodate the reentry device;
inserting a portion of the reentry apparatus into a blood vessel comprising an occlusion;
navigating the portion of the reentry apparatus to the occlusion;
extending the portion of the reentry apparatus into layers that form a wall of the blood vessel;
navigating the portion of the reentry apparatus beyond the occlusion;

moving the inner catheter relative to the outer catheter so as to expose the expandable anchors for expansion, thereby forcing said distal portion to deflect downward;

extending the reentry device into the blood vessel at an area beyond the occlusion.

17. The method of claim 16 further comprising the steps of:

extending a second reentry device from an inner lumen of said inner catheter into the blood vessel at an area beyond the occlusion.

18. The method of claim 17 further comprising the steps of:

passing a guidewire through the second reentry device.

* * * * *